(12) United States Patent
Brinkhues

(10) Patent No.: US 7,691,308 B2
(45) Date of Patent: Apr. 6, 2010

(54) METHOD AND DEVICE FOR PRODUCING A PHARMACEUTICAL SYRINGE PISTON STOPPER

(75) Inventor: Jurgen Brinkhues, Aachen (DE)

(73) Assignee: West Pharmceutical Services Deutschland GmbH & Co. KG, Eschweiler (DE)

( * ) Notice: Subject to any disclaimer, the term of this patent is extended or adjusted under 35 U.S.C. 154(b) by 255 days.

(21) Appl. No.: 11/620,070

(22) Filed: Jan. 5, 2007

(65) Prior Publication Data

US 2007/0107204 A1 May 17, 2007

Related U.S. Application Data

(60) Division of application No. 10/706,122, filed on Nov. 12, 2003, now Pat. No. 7,547,297, and a continuation of application No. PCT/EP02/04831, filed on May 2, 2002.

(30) Foreign Application Priority Data

May 11, 2001 (DE) ................. 101 22 959

(51) Int. Cl.
*B29C 65/00* (2006.01)
(52) U.S. Cl. .................................. 264/241
(58) Field of Classification Search .......... 425/521; 264/235, 241
See application file for complete search history.

(56) References Cited

U.S. PATENT DOCUMENTS

| | | |
|---|---|---|
| 1,652,156 A | 12/1927 | Beauchamp |
| 2,842,127 A | 7/1958 | Everett et al |
| 2,895,773 A | 7/1959 | McConnaughey |
| 3,263,011 A * | 7/1966 | Jagger et. al. ............ 264/153 |
| 3,470,291 A | 9/1969 | Johnson |
| 3,528,330 A | 9/1970 | Elert |
| 4,301,936 A | 11/1981 | Percarpio |
| 4,397,706 A | 8/1983 | Allen et al. |
| 4,397,903 A | 8/1983 | Allen et al. |

(Continued)

FOREIGN PATENT DOCUMENTS

DE 1952899 1/1967

(Continued)

*Primary Examiner*—Joseph S Del Sole
*Assistant Examiner*—Lorraine Rios
(74) *Attorney, Agent, or Firm*—Panitch Schwarze Belisario & Nadel LLP

(57) ABSTRACT

A piston stopper (2) made substantially of rubber has a piston section (8) enclosed in cap-like manner by an inert film (9) located adjacent to and facing the contents of a syringe or carpule cylinder (1). A non-vulcanized rubber sheet (7) is inserted into a form tool, together with an inert film (9). Under the effect of pressure and heat, an entire piston stopper contour is formed from the layered arrangement, extending to a flange (16) which protrudes laterally beyond the piston stopper (2) in the region of the separating plane of the form tool. A receiving cavity (6) for a piston rod is created in the piston section (8). The wall area of the sealing section (10) surrounding the receiving cavity (6) is forced into the receiving cavity (6). The piston stopper (2) is subsequently separated from the flange (16) in a blanking process, whereby a peripheral sealing area (13), directly adjacent to the edge of the inert film (9) enclosing the piston section (8), is formed in the sealing section (10).

6 Claims, 12 Drawing Sheets

U.S. PATENT DOCUMENTS

| | | | |
|---|---|---|---|
| 4,554,125 A * | 11/1985 | Knapp | 264/266 |
| 4,820,278 A | 4/1989 | Balisky | |
| 5,472,431 A | 12/1995 | Godat et al. | |
| 5,489,266 A | 2/1996 | Grimard | |
| 5,904,891 A | 5/1999 | Mizuno | |
| 5,948,341 A * | 9/1999 | Diamond et al. | 264/335 |
| 6,165,402 A | 12/2000 | Gabbard et al. | |
| 6,626,870 B1 | 9/2003 | Yarborough et al. | |

FOREIGN PATENT DOCUMENTS

| | | | |
|---|---|---|---|
| EP | 0148426 | A2 | 7/1984 |
| EP | 0148426 | * | 7/1985 |
| EP | 0204486 | B1 | 12/1986 |
| EP | 0205312 | A1 | 12/1986 |
| EP | 0375778 | A1 | 7/1990 |
| EP | 1020277 | A1 | 7/2000 |
| FR | 2074704 | | 10/1971 |
| GB | 593531 | A | 10/1947 |
| JP | 6-343677 | A | 12/1994 |
| JP | 8-182760 | A | 7/1996 |
| JP | 08182760 | A | 7/1996 |
| JP | 11029160 | AA | 2/1999 |
| JP | 2000218645 | * | 2/2000 |
| WO | 84/03682 | A1 | 9/1984 |
| WO | 95/24301 | A1 | 9/1995 |

* cited by examiner

US 7,691,308 B2

METHOD AND DEVICE FOR PRODUCING A PHARMACEUTICAL SYRINGE PISTON STOPPER

CROSS-REFERENCE TO RELATED APPLICATIONS

This application is a division of U.S. application Ser. No. 10/706,122, filed Nov. 12, 2003, which is a continuation of International Application No. PCT/EP02/04831, filed May 2, 2002, the disclosure of which is incorporated herein by reference.

BACKGROUND OF THE INVENTION

The invention is directed to a method for producing a pharmaceutical piston stopper made substantially from rubber or a similar elastomer, which has a receiving cavity for connecting with a piston rod or a similar displacement transferring element and a piston section enclosed in a cap-like manner by a fluorinated polymer film or similar inert film. The piston section in the working position faces the contents of a syringe or carpule cylinder and abuts on the outer circumference with its inert film against the syringe or carpule cylinder. The piston stopper has an uncoated sealing section adjacent to this piston section which in the working position abuts against the syringe or carpule cylinder. In a forming operation a layered arrangement comprising a non-vulcanized rubber sheet and a fluorinated polymer film or a similar inert film is placed into a forming tool and is formed into a piston stopper under the influence of pressure and heat, whereby the rubber sheet is vulcanized and joined with the inert film in a non-detachable manner.

In addition, the invention is directed to a device to produce pharmaceutical piston stoppers made substantially from rubber or a similar elastomer, which have a receiving cavity for connecting with a piston rod or a similar displacement transferring element and a piston section which, in the working position, faces the contents of a syringe or carpule cylinder and is enveloped in a cap-like manner by a fluorinated polymer film or a similar inert film. The piston section abuts on the outer circumference with its inert film against the syringe or carpule cylinder. The piston stopper has adjacent to this piston section an uncoated sealing section which abuts in the working position against the syringe or carpule cylinder. A forming tool forms the piston stopper from a layered arrangement comprising a non-vulcanized rubber sheet and a fluorinated polymer film or a similar inert film, wherein the forming tool has at least one first die plate and a second die plate interacting with the former, which can be displaced relative to one another into closed and open positions. A blanking device separates the piston stoppers from a layered arrangement flange laterally projecting beyond the piston stoppers and remaining in the region of the partition plane of the forming tool.

The invention is further directed to a pharmaceutical piston stopper, which has a base body made from rubber or a similar elastomer, a receiving cavity for connecting a piston rod or a similar displacement transferring element and a piston section enveloped by a fluorinated polymer film or similar inert film. The piston section, in the working position, faces the contents of a syringe or carpule cylinder and abuts with its inert film on the outer circumference against the syringe or carpule cylinder. The piston stopper has an uncoated sealing section adjacent to this piston section, the uncoated sealing section abutting in the working position against the syringe or carpule cylinder, and has at least one continuous sealing lip on its outer circumference.

When storing medications or pharmaceutical preparations, as a rule in liquid or powdery form, in the pre-filled syringe or carpule cylinders, varying requirements are placed on the piston stoppers to be used. Thus, a chemical or biological compatibility with the contents of the syringe or carpule cylinder is required, which on the one hand means that the substances contained in the material of the piston stopper must not leach into the medication situated in the syringe or carpule cylinder and contaminate it or alter its therapeutical effect. On the other hand, however, no active substances of the medication must penetrate into the piston stopper, because with increasing storage periods the concentration of the active substance in the medication would decrease. Finally, substances that penetrate from the medication into the piston stopper may also alter the functional properties of the piston stopper. Moreover, the piston stopper must seal the interior of the syringe or carpule cylinder against gas, liquid and germs.

From European published patent application EP 0 148 426 A1, a piston stopper made substantially from rubber is already known, which has a piston section which in the working position faces the contents of the syringe cylinder and is enveloped in a cap-like manner by an inert film and on its outer circumference has a continuous sealing lip coated with the inert film and abutting against the syringe cylinder. In this manner, the inert film should prevent a direct contact between the contents of the syringe cylinder and the rubber material that is incompatible with it. For the purpose of improving the sealing of the piston stopper against the syringe cylinder, adjacent to the coated piston section the piston stopper has a non-coated sealing section, which on its outer circumference has two parallel continuous sealing lips. In the working position these non-coated sealing lips abut against the syringe cylinder. Between the two sealing lips of the sealing section and between the uncoated piston section and the sealing lip of the sealing section adjacent to it a recess is respectively provided, by which the sealing lips are spaced from one another.

However, for pre-filled syringe systems, wherein the medication is stored in the syringe for a longer period, the piston stoppers are only conditionally suitable. The first sealing lip coated with the inert film seals only relatively poorly against the syringe cylinder. Due to this, it is possible that a portion of the medication in the syringe cylinder could leach through, between the first sealing lip and the wall of the syringe cylinder, into the recess situated between the first and the second sealing lip. During the administration of the medication this portion of the medication remains unused between the lamellae, as a result of which, for a syringe pre-filled with a specific quantity of a medication, the quantity of medication applied is correspondingly reduced. Moreover, the portion of the medication penetrated between the sealing lips of the piston stopper also comes into contact with the non-coated rubber material of the piston stopper, due to which the storage life of the medicinal contents of the syringe may be reduced.

The production of the known piston stopper is carried out in several operations. In the first operation for forming a first piston stopper portion with a piston section enveloped in a cap-like manner by the inert film, a non-vulcanized rubber sheet together with an inert film is pressed into a first hollow form of a caliper plate of a forming tool. There, the rubber sheet is vulcanized under the influence of pressure and heat and is non-detachably joined with the inert film. In a further operation the piston stopper portion thus formed is removed from the forming tool and blanked out from the coated rubber sheet. By doing so, the blanked out edge of the completed piston stopper forms the recess between the first sealing lip coated with the inert film and the second sealing lip adjacent to it. In a further operation the first piston stopper portion produced in this manner is placed into a hollow form of a second forming tool. Into this second forming tool a second non-vulcanized rubber sheet is placed, from which is formed, under the influence of pressure and heat, a second piston stopper portion, that is joined with the first piston stopper portion to provide the essentially complete piston stopper. During the forming in the second forming tool, a receiving cavity for connecting with the piston rod of a syringe is formed on the face of the piston stopper which is opposite to the inert film terminating at a spacing from the first piston stopper portion. Afterwards, the piston stopper is blanked out from the second rubber sheet.

The known method has the disadvantage that two forming operations and two blanking operations are necessary for the production of the piston stopper. Therefore, the method is relatively expensive. The method is also only conditionally suitable for a mass production. Although a plurality of the first piston stopper portions can be simultaneously formed in the first forming tool, they are, however, after their removal from the forming tool blanked out from the rubber sheet and then separated. The placing of the single piston stopper portions into a second forming tool, which has a number of forming cavities corresponding with the number of the piston stopper portions produced by the first forming tool, is therefore relatively complicated.

BRIEF SUMMARY OF THE INVENTION

Therefore, an object of the invention is to produce a piston stopper of the type mentioned at the outset, that can be simply and cost-effectively produced, that makes possible a better sealing of a syringe or carpule cylinder, and whereby an interaction between the material of the piston and the contents in the syringe or carpule cylinder is reliably prevented. There is the additional objective of providing a method and a device of the type mentioned at the outset, that makes possible a simple and cost-effective production of such a piston stopper.

The objective with regard to the method is achieved in that during the forming operation the complete contour of the piston stopper is formed from the layered arrangement up to the layered arrangement flange laterally protruding beyond the piston stopper and remaining in the region of the partition plane, that during the forming operation the receiving cavity is produced in the rubber sheet beyond the flange in the piston section enveloped in a cap-like manner by the inert film, that in a separating operation at least the wall region of the sealing section bordering the receiving cavity and protruding beyond the flange is displaced into the receiving cavity and the piston stopper is then separated from the flange by a blanking operation, so that in the sealing section an annular continuous sealing zone is formed that directly adjoins the edge of the inert film that envelopes the piston section in a cap like manner, the sealing zone in the working position abutting against the syringe or carpule cylinder.

Advantageously, this is possible by producing the piston stopper in only one forming operation and only one blanking or separating operation. In the forming operation the essentially complete contour of the piston stopper is formed from the layered arrangement, comprising the rubber sheet and the inert film. At the same time, the receiving cavity is produced in the rubber sheet at that end of the piston stopper which is opposite the inert film and beyond the surface plane coated with the inert film of the flange protruding laterally beyond the piston stopper. Therefore, the wall region of the sealing section that borders the receiving cavity can be displaced into the receiving cavity by the blanking or cutting tool during the blanking of the flange from the piston stopper. By virtue of this, it is possible to separate the flange from the piston stopper in such a manner, that in the sealing section of the piston stopper an annular continuous sealing zone is formed that is directly adjacent to the edge of the inert film enveloping the piston section in a cap-like manner, the sealing section being aligned with the edge region of the inert film or slightly protruding beyond it with the inert film in the working position abutting against the syringe or carpule cylinder. Thus, in the working position the piston stopper is sealed against the wall of the syringe or carpule cylinder by the sealing zone directly adjoining the inert film, due to which a contact of the contents of the syringe or carpule cylinder with the uncoated regions of the piston stopper, situated behind the sealing zone, is reliably prevented.

In the case of an advantageous embodiment of the invention, during the forming operation at least one annular continuous sealing lip is formed on the outer circumference of the sealing section. In this case, the piston stopper produced in accordance with the method seals in the working position even better against the wall of the syringe and carpule cylinder. Due to this, particularly the penetration of gases and/or germs into the contents of the syringe or carpule cylinder is basically made more difficult. In addition, the sealing lip makes possible an easy sliding of the piston stopper in the syringe or carpule cylinder. By virtue of the sealing zone formed during the separating operation, it will be impossible for the contents of the syringe or carpule cylinder to reach the intermediate space between the sealing lip and the piston section enveloped by the inert film and impossible for an interaction to occur therein with the elastomeric piston material.

An advantageous embodiment of the invention provides that in the separating operation the at least one piston section enveloped in a cap-like manner by the inert film is placed centered into an opening of a cutting die, and the flange bordering the piston stopper is clamped between this cutting die and a clamping plate, while the portion of the sealing section which projects beyond the flange engages a pass-through opening provided in the clamping plate, and that afterwards the wall region of the sealing section bordering the receiving cavity of the piston stopper is displaced by a cutting punch into the receiving cavity, and the flange is blanked off the piston stopper. The piston stopper is then placed into the opening of the cutting die with its piston section centered relative to the longitudinal axis of the cutting tool and during the blanking operation it is fixed in the centered position via the flange clamped between the cutting die and the blanking plate. The portion of the sealing section that engages the pass-through opening of the blanking plate and abuts against its wall is additionally centered in the pass-through opening relative to the cutting tool. The wall region of the sealing section bordering the receiving cavity can be easily displaced then into the receiving cavity by the cutting tool during its forward blanking movement.

It is particularly advantageous if the cutting punch to separate the piston stopper from the flange is moved in the direction from the free end of the sealing section towards the flange. In this case the wall region of the piston stopper bordering the receiving cavity can be even better displaced into the receiving cavity.

A particularly advantageous embodiment of the invention provides that the rubber sheet is continuously sealed on its outer edge against at least one die plate of the forming tool resting on it and that during and/or after the opening of the forming tool to release the vulcanized layered arrangement from the die plate a gas is injected between this die plate and the layered arrangement. The vulcanized layered arrangement is then evenly acted upon by the pressure of the injected gas prior to the removal from the die plate, making a gentle removal of the layered arrangement possible. An excess stretching of the vulcanized rubber and/or of the inert film is prevented by this. Consequently, the piston stoppers produced in accordance with the method keep their dimensions very well, making the placing of the vulcanized layered arrangement into the cutting die particularly possible.

It is advantageous when, for the sealing of the vulcanized layered arrangement against the die plate during the forming operation, a seal is formed on the outer edge of the layered arrangement, tightly abutting against the die plate and continuous around the layered arrangement. Therefore, the seal necessary for the sealing of the rubber sheet is produced together with the piston stopper(s) in one operation. Consequently, the method can be carried out even more simply.

The objective mentioned above with regard to the device is achieved in that the forming tool is constructed for the forming of the complete contour of at least one piston stopper up to the flange remaining in the region of the partition plane of the forming tool and laterally protruding beyond the piston stoppers, and that for this purpose the first die plate has at least one first cavity fitting the form of the piston section of the piston stopper to be produced and the second die plate has at least one second cavity fitting the form of the uncoated sealing section of the piston stopper, that in the second cavity a form core is provided to form a receiving cavity of the piston stopper that can be connected with the piston rod or a similar displacement transferring element, the form core engaging with its free end the opposite situated first cavity in the closed position of the forming tool, that the blanking device has a cutting die with at least one orifice for the central placement of the piston section enveloped in a cap-like manner by the inert film, that a sleeve-shaped cutting punch having a cutting edge on its outer circumference is allocated to the cutting die to separate the flange from the piston stopper, the cutting punch being able to move axially towards and away from the orifice of the cutting die, and that the inside cavity of the cutting punch is constructed to accommodate the inwardly deformed sealing section of the piston stopper.

In an advantageous manner, the device makes possible the production of the piston stoppers in a single forming operation and a single punching operation. Because the form core, protruding in the cavity of the second die, that in the working position abuts against the rubber sheet to form the receiving cavity of the piston stopper that can be connected with a piston rod or a similar displacement transferring element, in the closed position of the forming tool engages with its free end the opposite situated cavity of the first die plate that in the working position abuts against the inert film, the receiving cavity is formed during the forming of the piston stopper in the forming tool up into the piston section enveloped in a cap-like manner by the inert film. The vulcanized layered arrangement, comprising the rubber sheet and the inert film, after the removal from the forming tool is placed centered with the piston section enveloped in a cap-like manner by the inert film into the opening of the cutting die. During the forward movement of the sleeve-shaped cutting punch, that can be axially displaced relative to this opening, the wall region of the piston laterally bordering the receiving cavity is inwardly deflected transversely to the feed movement and is pushed into the inside cavity of the cutting punch. For this reason, it is possible to push the cutting punch onto the free end of the sealing section of the piston stopper without damaging it. In a further progression of the forward blanking movement of the cutting punch, the cutting punch pierces the flange laterally protruding beyond the piston stopper and separates it from the piston stopper. At this time, an annular sealing zone is formed, continuous around the sealing section, which in the working position abuts against the syringe or carpule cylinder. The dimensions of the outer cross-section of the cutting punch, that has a cutting edge on its outer circumference, correspond to the cross-sectional dimensions of the orifice of the cutting die or are somewhat smaller than those. The cross-sectional dimensions of the cavity of the first die plate to form the piston section enveloped in a cap-like manner and consequently the cross-sectional dimensions of this piston section correspond approximately to those of the orifice of the cuffing die. Therefore, in the case of the complete piston stopper, the sealing zone, directly adjacent to the inert film and continuous around the sealing section, is aligned with the edge region of the inert film, which in the working position abuts against the syringe or carpule cylinder or radially protrudes slightly beyond it, as a result of which the sealing section reliably seals against the syringe or carpule cylinder.

For the simultaneous forming of a plurality of piston stoppers, the die plates of the forming tool can have a number of cavities that corresponds to the number of piston stoppers to be formed. In that case, the cutting die of the blanking device can have a number of orifices that corresponds to the number of cavities of a die plate with a cutting punch provided above each of them, while the arrangement of the orifices corresponds to that of the cavities of the die plate, so that the vulcanized layered arrangement can be placed into the cutting die for the simultaneous blanking of all piston stoppers provided on it with the piston sections enveloped in a cap-like manner.

An advantageous embodiment of the device according to the invention provides that the stamping device has a clamping plate with at least one pass-through orifice that is aligned with one of the at least one opening of the cutting die to accommodate the sealing section, that for the purpose of clamping the flange between the clamping plate and the cutting die the clamping plate is axially displaceable towards the opening of the cutting die relative to the cutting die, and that the cutting punch is axially displaceably guided in the pass-through orifice of the clamping plate.

In the case of an advantageous embodiment of the invention, the circumferential wall of the at least one cavity of the second die plate has at least one annular continuous recess to form an annular continuous sealing lip on the outer circumference of the piston stopper's sealing section. The piston stoppers produced with the forming tool then seal even better against the syringe or carpule cylinder.

In a useful manner, the cutting punch has an entry slope on its inner side at its free end facing the cutting die. The wall of the piston stopper, bordering the receiving cavity, can then be more easily displaced during the blanking movement of the sleeve-shaped cutting punch into the inside cavity of the cutting punch.

A particularly advantageous embodiment of the invention provides that the outer edge of the vulcanized layered arrangement can be sealed against at least one die plate by means of a continuous seal around the layered arrangement, and that a gas supply channel opens into the region of this die plate bordered by the seal, the gas supply channel being connected to a source of pressurized gas for detaching the layered arrangement from the die plate. The vulcanized layered arrangement with the syringe piston(s) formed on it can then be simply removed from the second die plate by the gas pressure. At the same time, the gas pressure makes possible an even and gentle detaching of the layered arrangement from the die plate. This is of particularly advantage when the cavity (cavities) of the die plate has (have) recesses that engage the layered arrangement.

It is advantageous if at least one die plate for the formation of the seal sealing the outer edge of the layered arrangement against the die plate has inside its form cavity an annular groove bordering the cavity (cavities) of this die plate at a distance. In this case, the seal is formed on the edge of the layered arrangement preferably on the rubber sheet during the forming of the piston stopper(s).

In a useful manner, a valve is provided in the entry region of the gas supply channel, preferably a disc valve. The gas supply channel is then sealed by the valve during the forming of the piston stopper, so that the elastomer and/or the inert film cannot penetrate into the gas supply channel.

The above mentioned objective with regard to the pharmaceutical piston stopper is achieved in that the base body is made from one piece, that the receiving cavity extends up into the piston section that is enveloped in a cap-like manner by the inert film, and that on its outer circumference the sealing section has an annular continuous sealing zone that is directly adjacent to the edge of the inert film enveloping the piston section in a cap-like manner, the sealing section in the working position abutting flat against the syringe or carpule cylinder.

Accordingly, in the working position the piston stopper is sealed by the sealing zone against the wall of the syringe or carpule cylinder directly where the inert film joins it, due to which a contact of the contents of the syringe or carpule cylinder with the uncoated regions of the piston stopper situated behind the sealing zone is reliably prevented. Because the base body is made from one piece, the piston stopper can be produced simply and cost-effectively from a single rubber sheet coated with an inert film.

It is advantageous if the sealing zone is provided as a straight extension to the outer circumferential section of the inert film, that in the working position abuts against the syringe or carpule cylinder or slightly projects beyond this outer circumferential section. In this case, in the working position the sealing zone seals against the wall of the syringe or carpule cylinder directly adjoining the inert film.

In the case of a useful embodiment of the invention, a section of the inside wall of the piston stopper bordering the receiving cavity has an internal thread to connect with the thread of the piston rod or a similar displacement transferring element, while this section of the internal thread terminates at a spacing from the bottom of the receiving cavity. In this case, the piston stopper can be joined or screwed together with the piston rod or the displacement transferring element in a form-locking manner. The piston stopper then can be produced in a forming tool from a layered arrangement, comprising a non-vulcanized rubber sheet and a fluorinated polymer film or a similar inert film, and can be easily removed afterwards from the forming tool.

An advantageous embodiment of the invention provides that the section of the piston stopper with the internal thread terminates at the piston section enveloped in a cap-like manner or at a spacing from it, and that preferably a cylindrical or tapered receiving cavity joins the section with the internal thread, the receiving cavity extending into the piston section enveloped in a cap-like manner. In this case it is even easier to remove the piston stopper from the forming tool during production.

Another embodiment of the invention provides that the cross-section of the receiving cavity commencing from the bottom tapers out towards the opening of the receiving cavity. This piston stopper, intended to be connected with the piston rod of a carpule, is also easier to remove from the forming tool during its production.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 10:
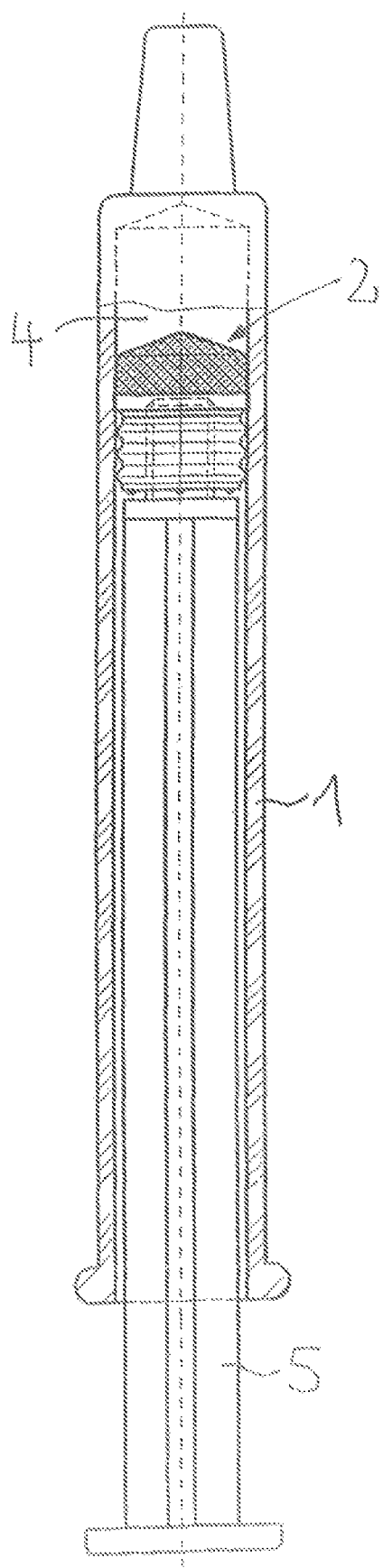
FIG. 10 is a schematic, side view (partially sectioned) of a syringe having a piston according to the invention.
Figure 12:
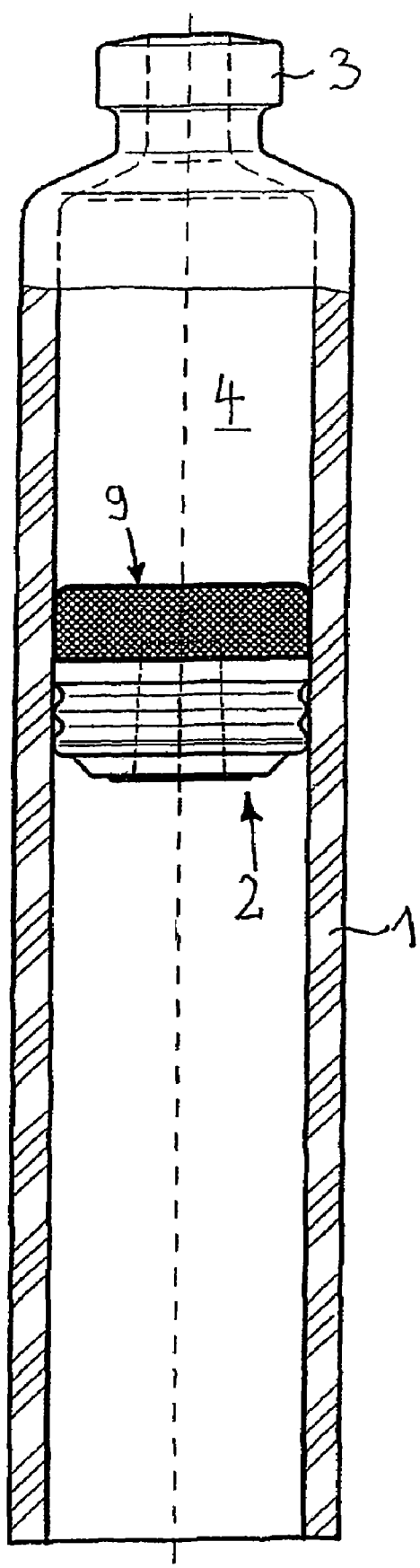
FIG. 12 is a schematic, side view (partially sectioned) of a carpule according to the invention.

As shown in FIGS. 10 and 12, for example, a pharmaceutical syringe or carpule has a syringe or a carpule cylinder 1 with a piston stopper 2 that can be axially displaced therein. The syringe or carpule cylinder 1 has at one end a discharge orifice for a liquid pharmaceutical preparation situated in the cylindrical cavity 4 of the syringe or carpule cylinder 1, the discharge orifice being tightly closed off by a removable cover 3. The syringe or carpule cylinder 1 has a pass-through opening at that end, which is situated opposite the discharge orifice for a piston rod 5 joined with the piston stopper 2, the piston rod engaging a receiving cavity 6 of the piston stopper 2 with its end facing the receiving cavity.

Figure 9:
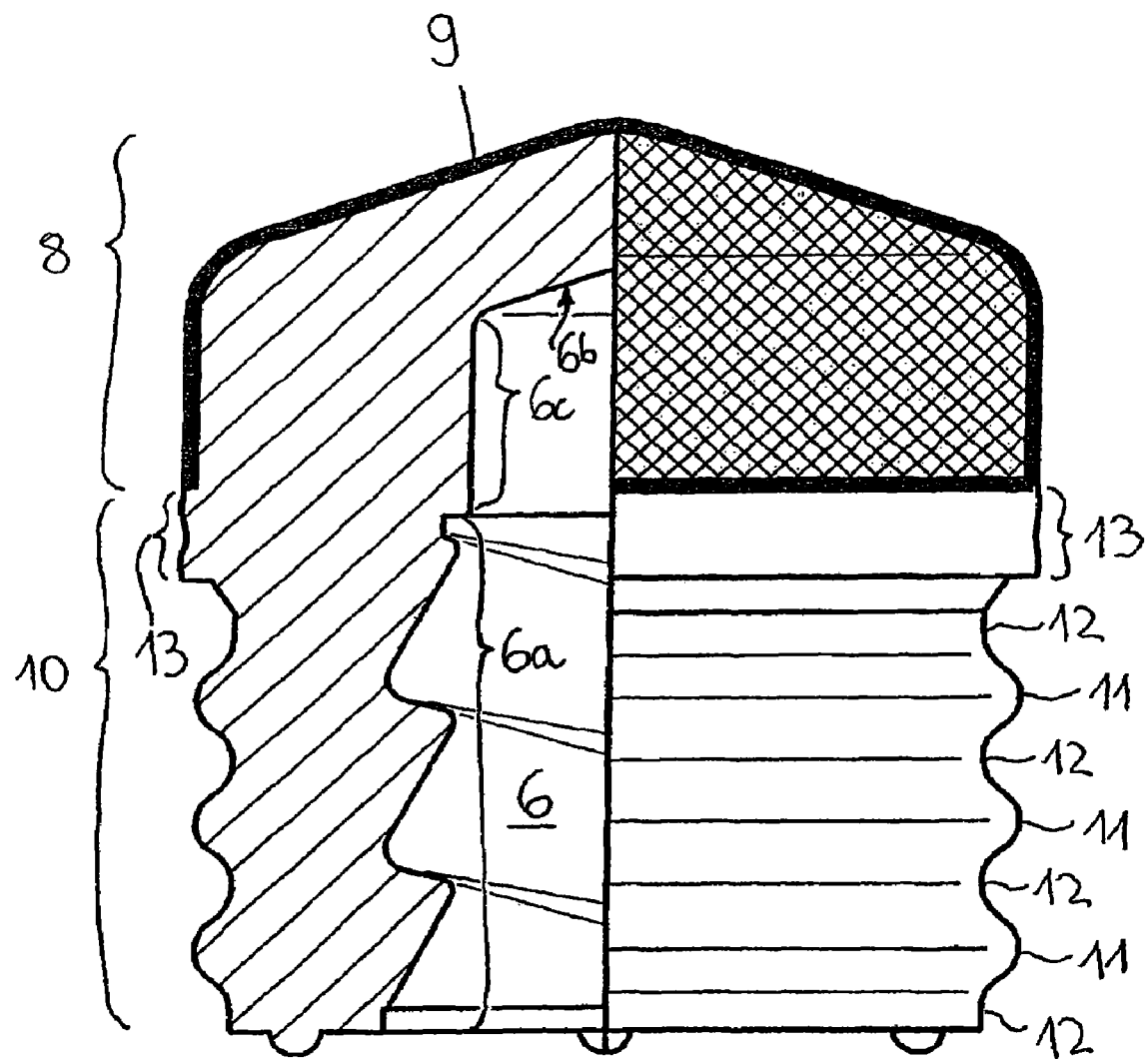
FIGS. 9 and 11 are schematic side views, partially sectioned, of a pharmaceutical piston stopper according to the present invention.
Figure 11:
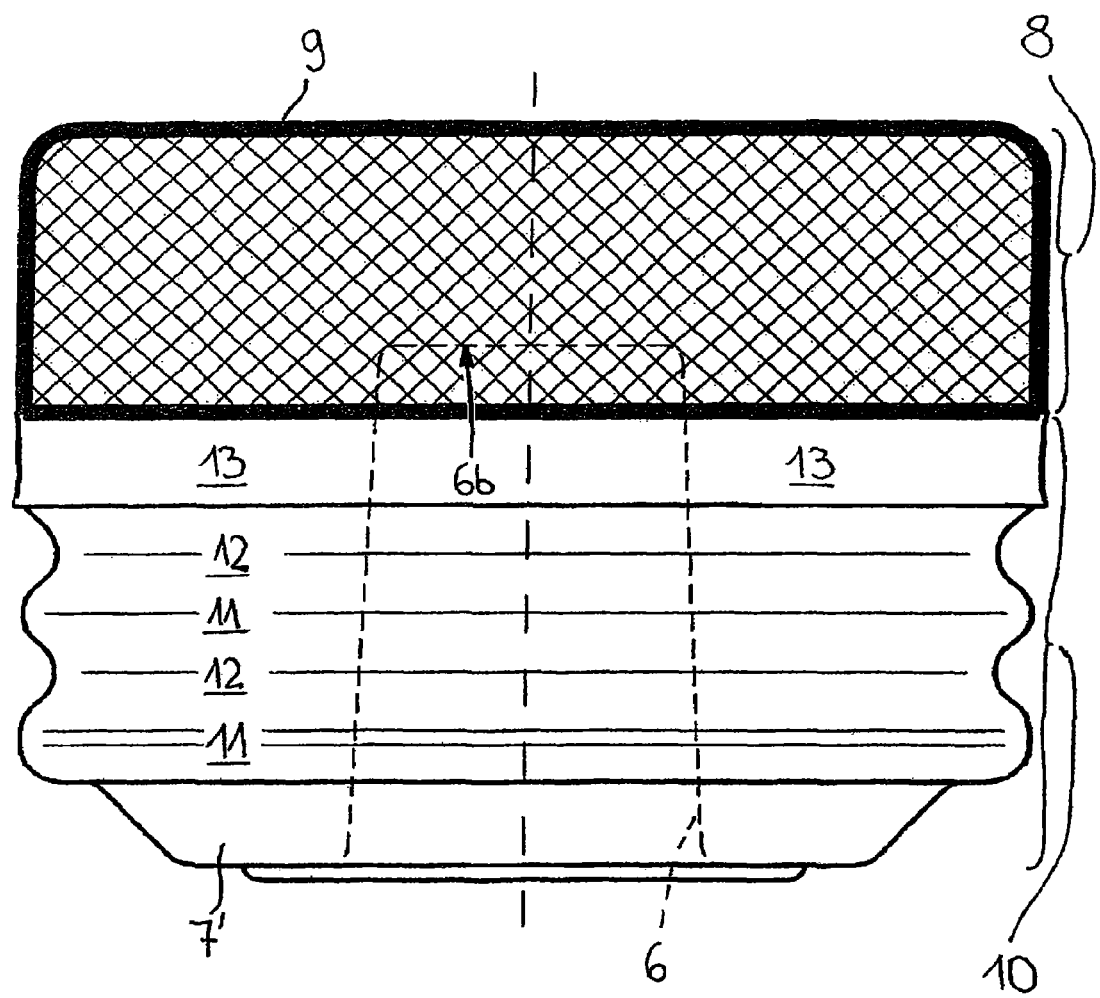

As it can be particularly well seen in FIGS. 9 and 11, the piston stopper 2 has a single-piece base body 7' made from rubber or a similar elastomer, that is enveloped in a cap-like manner by a fluorinated polymer film or a similar inert film 9 on a section 8 of the piston which faces the contents of the syringe or carpule cylinder 1. A non-coated sealing section 10 of the piston stopper 2 is adjacent to this piston section 8. It can be seen in FIGS. 10 and 12 that on its outer circumference the piston stopper 2 abuts against the inside wall of the carpule cylinder 1 with both the edge region of the inert film 9 and the sealing section 10.

On its outer circumference the sealing section 10 has a plurality of continuous sealing lips 11, that are spaced from one another by continuous recesses 12 situated between them on the outer circumference of the sealing section 10. A recess 12 is also provided between the inert film 9 and the sealing lip 11 adjacent to the inert film 9. Between this recess 12 and the inert film 9 the sealing section 10 has on its outer surface an annular continuous sealing zone 13, that adjoins directly the edge of the inert film 9. The sealing zone 13 is aligned with the surface of the edge region of the inert film 9 abutting against the inside wall of the syringe or carpule cylinder 1 or projects slightly radially beyond this surface. In the working position the piston stopper 2 abuts with the sealing zone 13 fully against the syringe or carpule cylinder 1. Due to this the recesses 12 are reliably sealed against the liquid pharmaceutical preparation situated in the cylindrical cavity 4, so that the preparation cannot interact there with the elastomer. Consequently, the sealing zone 13 prevents the penetration into the adjacent recess 12 of the pharmaceutical preparation between the inert film 9, with a poorer sealing than that of the non-coated elastomer, and the inside wall of the syringe or carpule cylinder 1. Moreover, the sealing zone 13 also seals the pharmaceutical preparation against the penetration of moisture, gases and/or germs. In addition, the cylindrical cavity 4 is sealed by the sealing lips 11 that are in a series with the sealing zone 13.

As can be seen from FIGS. 9 and 11, the receiving cavity 6 extends from the receiving orifice situated at that end region of the piston stopper 2 that is remote from the inert film 9 up into the piston section 8 and terminates there at a distance from the inert film 9.

In the embodiment according to FIG. 9, a section 6a of the receiving cavity has an internal thread, which can be screwed together with a matching external thread of the piston rod 5. The section 6a of the piston stopper 2 with the internal thread extends within the region of the piston limited by the non-coated sealing section 10 and terminates at a distance from the piston section 8. Section 6a with the internal thread is joined by an approximately cylindrical receiving cavity section 6c, which extends up into the piston section 8 and terminates at section 6b. However, other form-locking connections between the piston stopper 2 and the piston rod 5 or similar displacement transferring element are also conceivable. In the embodiment according to FIG. 11 the receiving cavity has, for example, a tapered shape and it tapers commencing from its receiving orifice towards the deepest position of the receiving cavity 6.

Figure 1:
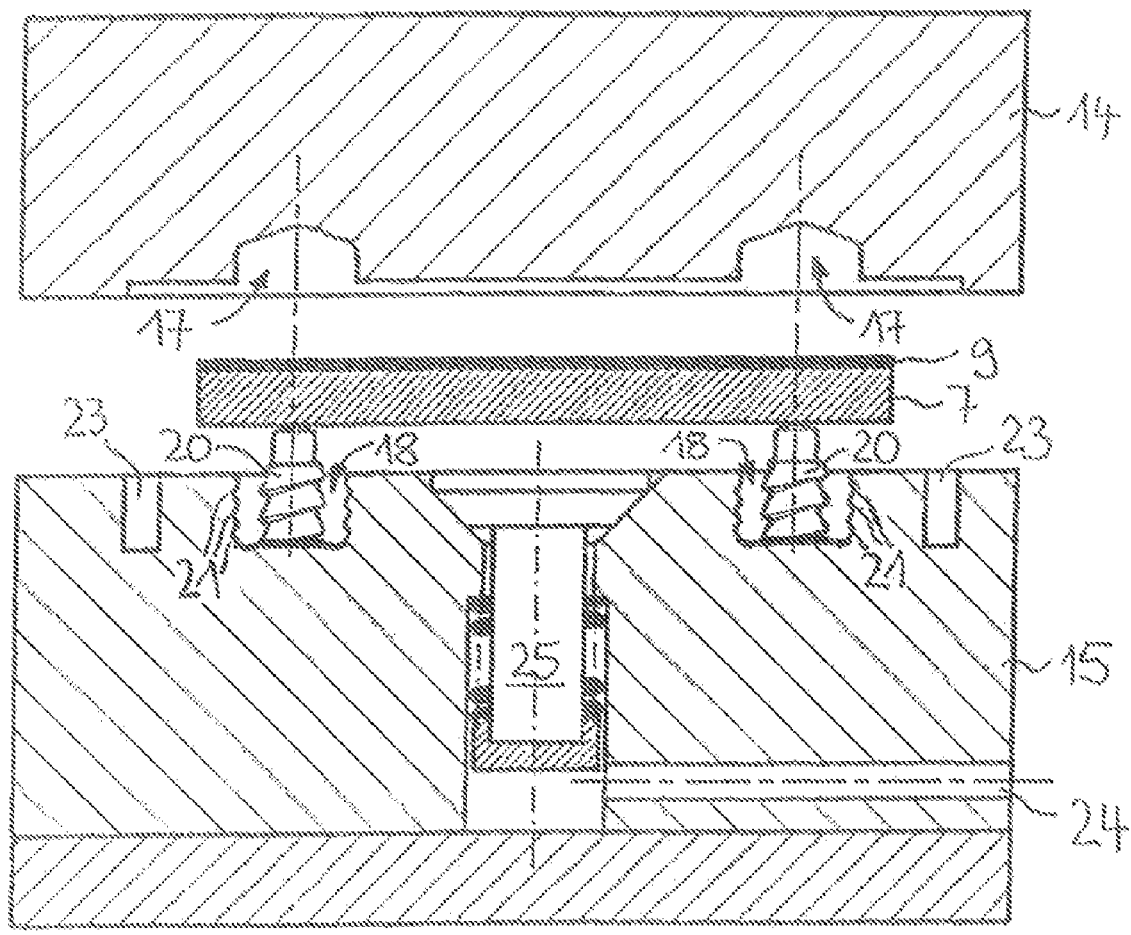
FIG. 1 is a schematic, cross-sectional view through a forming tool in the open position, into which is placed a rubber sheet, coated on one side with an inert film, according to the invention.

As shown in FIGS. 1-8, for the production of the piston stopper 2, first a non-vulcanized rubber sheet 7, together with a fluorinated polymer film or a similar inert film 9 is placed between the die plates 14, 15 of a forming tool. The die plates 14, 15 can be displaced relative to one another and can be brought to a closed position (FIG. 2) and an open position (FIG. 1). As is shown in FIG. 1, the foil-like inert film 9, which is initially flat, can be firmly joined with the rubber sheet 7. However, the inert film 9 and the rubber sheet 7 may be introduced between the die plates 14, 15 independently from one another and placed loosely on top of one another.

The forming tool is constructed to form the complete contour of the piston stopper 2 up to the layered arrangement flange 16 remaining in the region of the partition plane of the forming tool and laterally projecting beyond the piston stopper 2. It can be seen in FIG. 1, that for this purpose the first die plate 14 facing the inert film 9 has a plurality of first cavities 17, the form of which corresponds to the negative form of the piston section 8 of the syringe piston 2 to be produced. The second die plate 15 facing the rubber sheet 7 has a plurality of second cavities 18, the number of which corresponds to the number of the first cavities 17, the form of which corresponds to the negative form of that portion of the syringe piston sealing section 10 which adjoins the sealing zone. The first and second cavities 17, 18 are aligned with one another, so that in the closed position of the forming tool they essentially define the outer contour of the syringe piston 2 to be produced. In the closed position of the forming tool the first and second cavities 17, 18 are spaced from one another by a separation gap 19, that extends in the partition plane over all cavities 17, 18 of the forming tool and joins these with one another. During the forming of the layered arrangement comprising the rubber sheet 7 and the inert film 9 the flange 16 is formed in the partition plane 19.

Figure 2:
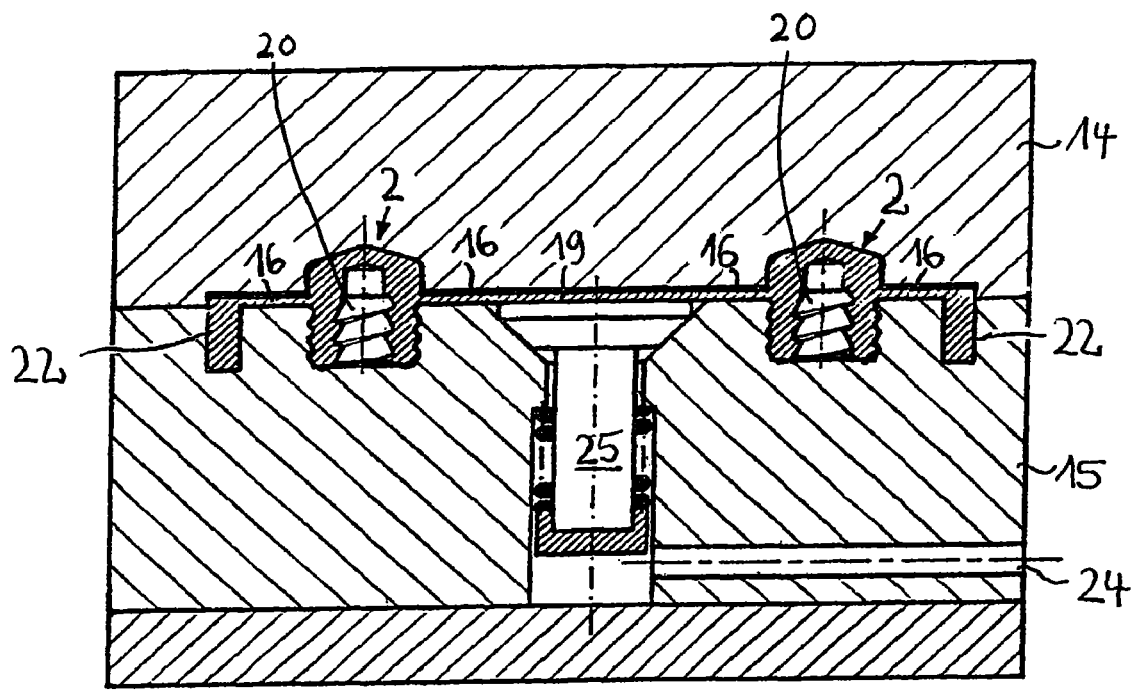
FIG. 2 is an illustration similar to that of FIG. 1, but with the forming tool closed.

As can be particularly well seen in FIG. 2, the second cavities limit a form core 20 each to form the receiving cavity 6 of the piston stopper 2 that can be connected with the piston rod 5. In the closed position of the forming tool this form core 20 engages with its free end the opposite situated first cavity 17, so that during the forming of the piston stopper 2 the receiving orifice 6 is brought up into the piston section 8 of the piston stopper 2. The circumferential walls of the second cavities 18 have annular continuous depressions 21 to form the annular continuous sealing lips 11 on the outer surface of the piston stopper sealing section 10.

When the forming tool is closed, the rubber sheet 7 is vulcanized under the influence of pressure and heat and is non-detachably joined with the inert film 9. At the same time, the sections of the inert film 9 abutting against the walls of the first cavities 17 assume the form of the first cavities 17, and the sections of the rubber sheet 7 abutting against the walls of the second cavity 18 assume the form of the second cavities 18.

For the formation of a seal 22 that seals the outer edge of the vulcanized layered arrangement against the die plate 14, the second die plate 15 has inside its forming cavity a continuous groove 23 that borders the cavities 18 of this die plate 15 at a distance. During the closing of the forming tool the elastomer situated on the edge of the rubber sheet 7 is displaced into this annular groove 23, while it assumes the form of the annular groove 23.

The second die plate 15 has a gas supply channel 24, that opens into the form cavity formed between the die plates 14, 15 within the region bordered by the annular groove 23. After the completion of the forming process, compressed air is blown through this gas supply channel 24, the compressed air lifting the layered arrangement, comprising the vulcanized rubber sheet 7 and the inert film 9, off the second die plate 15. It can be seen in FIG. 3 that during the removal of the layered arrangement from the second die plate 15, assisted by the compressed air, the seal 22 initially remains engaged with the annular groove 23, so that between the rubber sheet 7 and the second die plate 15 an air cushion can be formed. At the same time, the forming tool is opened, so that during the opening the layered arrangement remains with its inert film 9 initially adhering to the first die plate 14, as can be recognized from FIG. 3. However, another course of action is also possible, whereby first the forming tool is opened and the first die plate 14 is removed from the layered arrangement, and afterwards the compressed air is blown between the layered arrangement and the second die plate 15. After detaching the layered arrangement from the second die plate 15, the layered arrangement is removed from forming tool. At this time the inert film 9 detaches itself from the first die plate 14 (FIG. 4).

Figure 3:
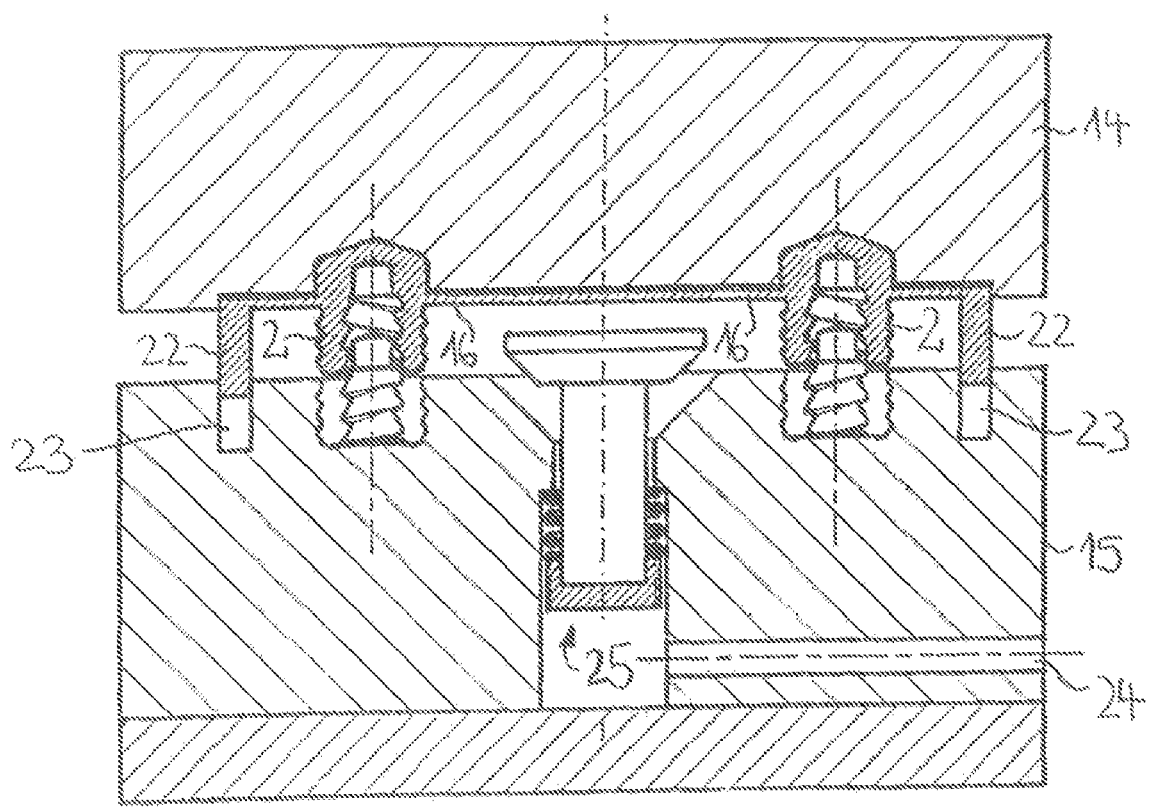
FIG. 3 is a schematic, cross-sectional view through the forming tool during the air-assisted removal of the layered arrangement comprising the vulcanized rubber sheet and the inert film.
Figure 4:
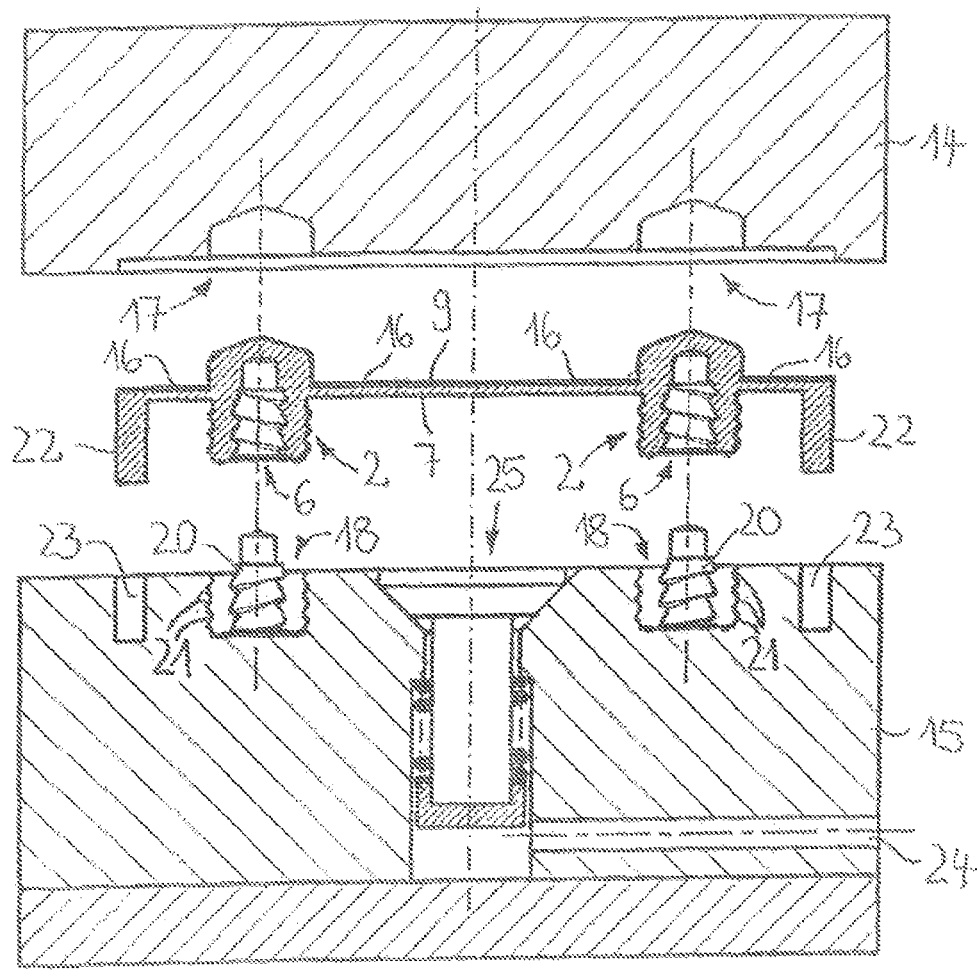
FIG. 4 is a schematic, cross-sectional view through the forming tool during the removal of the vulcanized layered arrangement.

As can be particularly well perceived from FIG. 3, in the entry region of the gas supply channel 24 a valve 25 is provided, whose valve head faces the first die plate 14. It can be clearly seen that the valve is provided outside the cavities 18 and is at a lateral spacing from them. The valve plate of the valve 25 is held in the closed position by a helical spring and can be lifted off its valve seat against the restoring force of the helical spring by the pressure of the compressed air that can be conveyed through the gas supply channel 24.

After its removal from the forming tool the layered arrangement is placed on a blanking device 26 (FIG. 5) to separate the piston plug 2 from the flange 16 surrounding it. The blanking device 26 has a cutting die 27, which is constructed as a plate with a number of orifices 28 that corresponds to the number of the first cavities 17. The diameter of these orifices 28 corresponds approximately to the diameter of the first cavities 17. The relative positions of the orifices 28 also correspond to the positions of the cavities 17 relative to one another. The layered arrangement is so arranged on the cutting die 27, that the individual piston sections 8 of the layered arrangement, enveloped by the inert film 9, engage centrally the orifices 28 associated with them and the flange 16 will lie on the cutting die 27.

Figure 6:
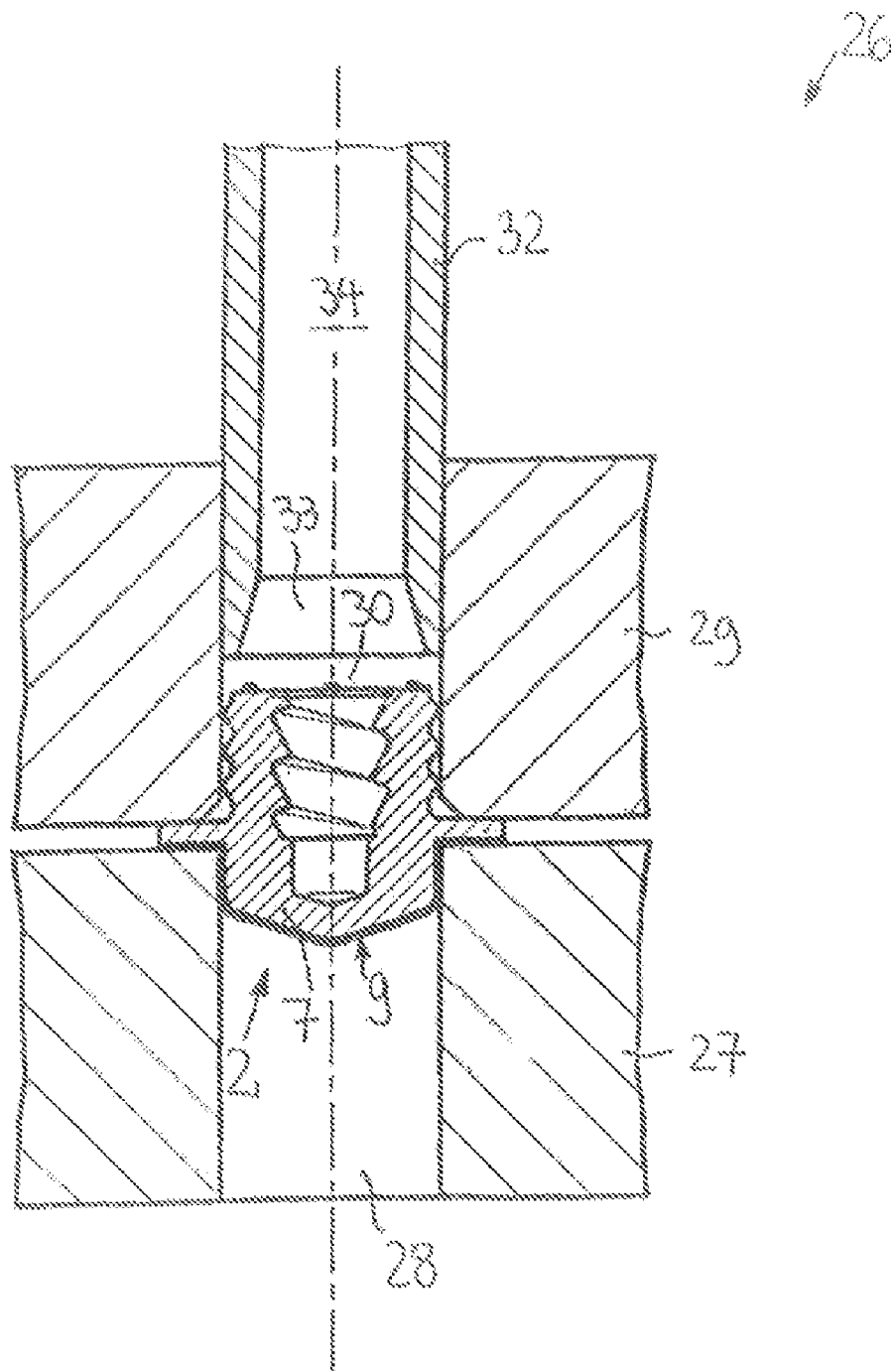
Figure 7:
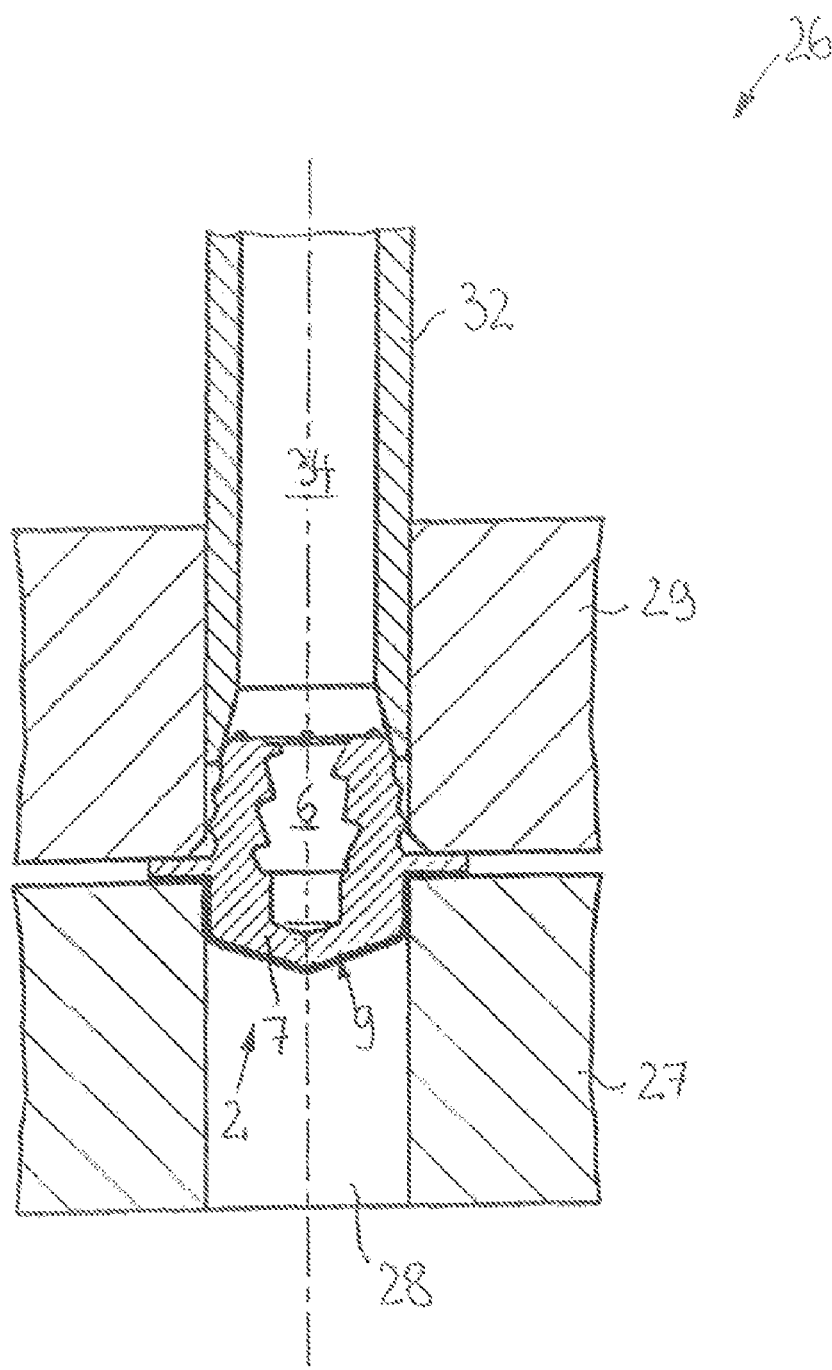

Parallel to the plane of the cutting die 27 a clamping plate 29 is provided, which has a number of pass-through openings 30 corresponding to the number of orifices 28 of the cutting die 27. The pass-through openings have the same diameter as the orifices 28 of the cutting die 27 and are aligned in a straight extension with the orifices 28. After placing the layered arrangement into the cutting die 27, the clamping plate 29 is moved towards the cutting die 27 until the flange 16 is clamped between the clamping plate 29 and the cutting die 27, and the piston stoppers 2 provided on it are thus fixed on the cutting die 27 (FIG. 6).

Figure 5:
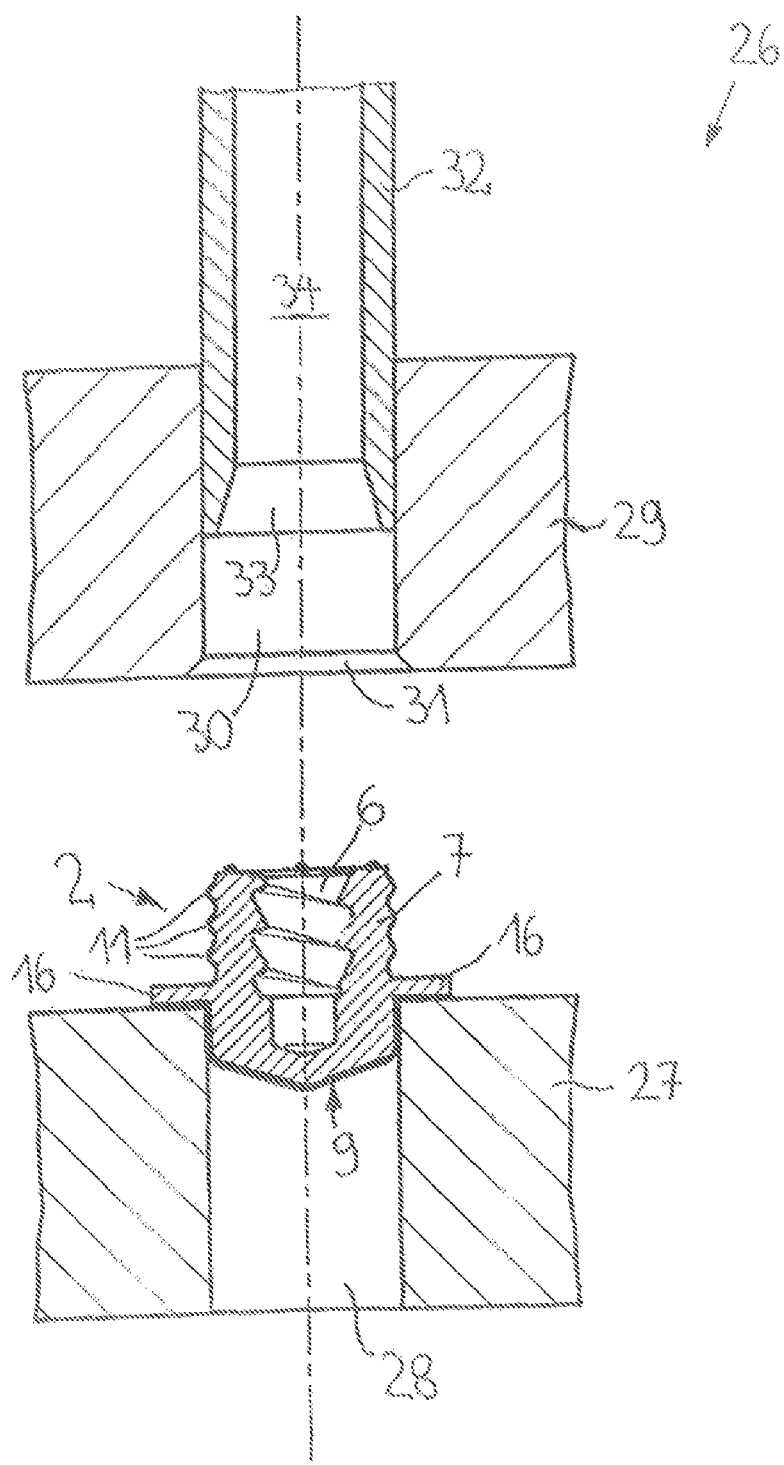
FIGS. 5-8 are schematic, partial cross-sectional views through a blanking device to separate a layered arrangement flange (only partially illustrated) that projects laterally from a piston stopper beyond the piston stopper, wherein the clamping plate and the punch of the blanking device are illustrated in various working positions.

From FIG. 5 it can be seen that at that end of the pass-through orifices 30 which face the cutting die 27 an entry slope 31 formed by a chamfer is provided for the sealing section 10 of the piston stopper 2 to be introduced into the pass-through opening 30. The sealing section 10 of the piston stopper 2 is centered by this entry slope 31 when the clamping plate 29 is moved towards the cutting die 27.

In each pass-through opening 30 a sleeve-shaped cutting punch 32 is axially displaceably guided, that has a cutting edge on its circumference. It can be seen from FIGS. 6 to 8 that, to separate the flange 16 from the piston stoppers positioned on the cutting die 27, the cutting punches 32 move towards the cutting die 27, and after the separation of the flange 16 they are pulled back to their initial position.

At their free ends facing-the cutting die 27 the cutting punches 32 have on their inside an entry slope 33. It can be seen from FIG. 7 that, during the forward cutting movement of the cutting punch 32, the wall of the piston stopper 2 bordering the receiving cavity 6 is displaced by its entry slopes 33 into the internal cavity 34 of the cutting punch 32. At the same time, the cross-section of the receiving cavity 6 is correspondingly reduced.

Figure 8:
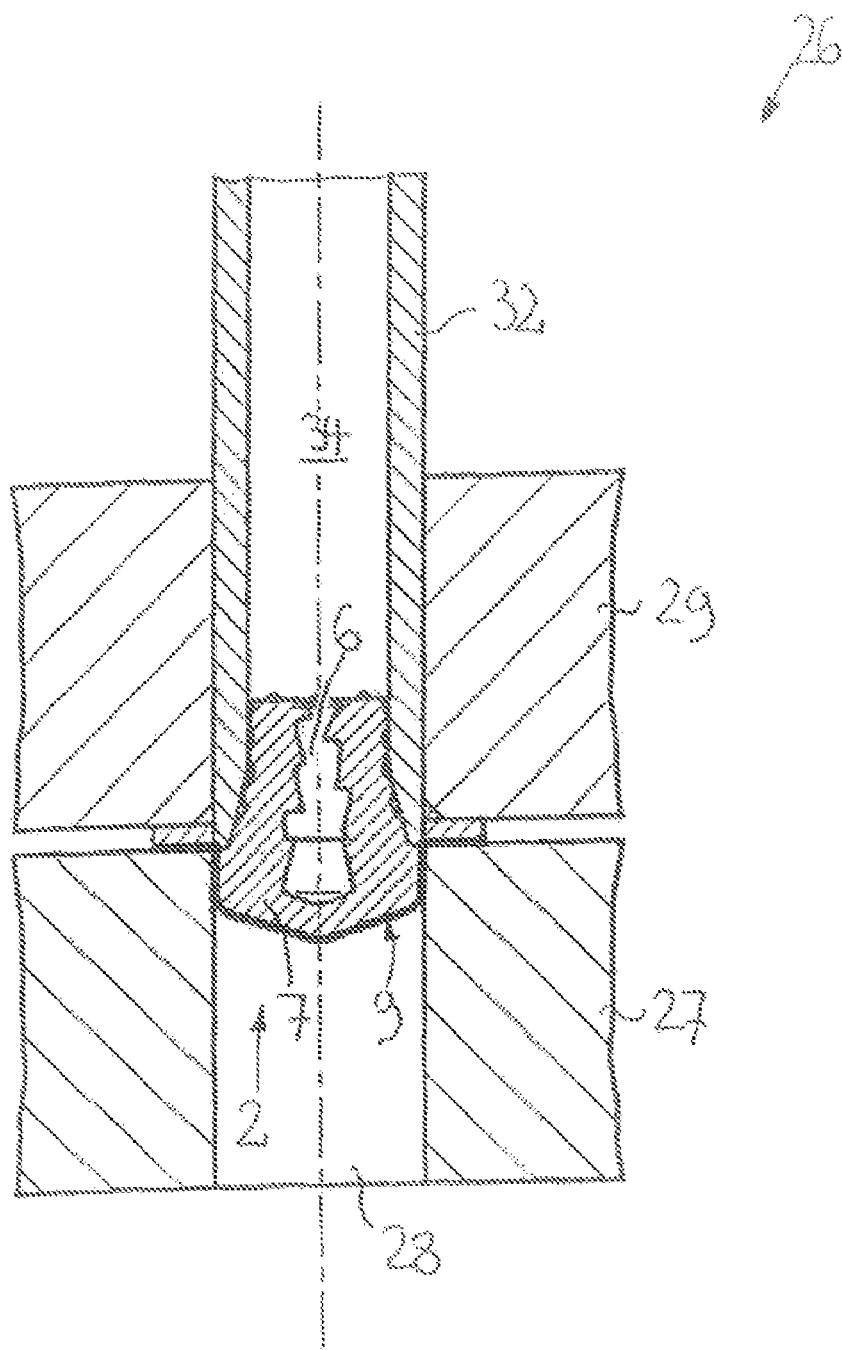

It can be seen from FIG. 8, that the diameter of the cutting punch 32 corresponds approximately to the diameter of the orifice 28 of the cutting die 27, so that the flange 16 is separated from the piston stopper 2 by the cutting punch 32 flush with the portion of the inert film 9 that, in the working position, abuts against the syringe cylinder 1. This forms the sealing zone 13.

Therefore, the invention concerns a piston stopper 2 made substantially from rubber, which has a piston section 8 enveloped in a cap-like manner by an inert film 9 and, in the working position, facing the contents of a syringe or carpule cylinder 1 and abutting with its inert film 9 against the syringe or carpule cylinder 1. Adjacent to this piston section 8 the piston stopper 2 has an uncoated sealing section 10. Furthermore, the invention concerns a device and a method for the production of such a piston stopper 2. A non-vulcanized rubber sheet 7, together with an inert film 9, is placed into a forming tool and, under the influence of pressure and heat the complete piston stopper contour is formed from this layered arrangement up to a flange 16 laterally projecting beyond the piston stopper 2 in the region of the separation plane. A receiving cavity 6 for a piston rod is formed up into the piston section 8. The wall region of the sealing section 10 bordering the receiving cavity 6 is displaced into the receiving cavity 6. Afterwards, the piston stopper 2 is separated from the flange by a blanking operation, whereby in the sealing section 10 a continuous sealing zone 13 is formed, which is directly adjacent to the edge of the inert film 9 enveloping the piston section 8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for producing a pharmaceutical piston stopper (2) made substantially from an elastomer and comprising a receiving cavity (6) for connecting with a displacement transferring element and a piston section (8) enclosed in a cap-shaped inert film (9), the piston section in a working position facing contents of a syringe or carpule cylinder (1), an outer circumference of the piston section with its inert film (9) abutting against the syringe or carpule cylinder (1), the piston stopper (2) having an uncoated sealing section (10) adjacent to the piston section (8), the method comprising:

placing a layered arrangement comprising a non-vulcanized rubber sheet (7) and an inert film (9) into a forming tool and forming the layered arrangement into a piston stopper under the influence of pressure and heat during a forming operation, wherein the rubber sheet (7) is vulcanized and joined with the inert film (9) in an non-detachable manner;

forming the complete contour of the piston stopper (2) during the forming operation from the layered arrangement up to a layered arrangement flange (16) protruding laterally beyond the piston stopper (2) and remaining in a region of a partition plane of the forming tool;

producing the receiving cavity (6) in the rubber sheet (7) beyond the flange (16) in the piston section (8) during the forming operation;

displacing at least a wall region of the sealing section (10) bordering the receiving cavity (6) and protruding beyond the flange (16) opposite the piston section (8) into the receiving cavity (6) during a separating operation; and separating the piston stopper (2) from the flange (16) by a blanking operation, so that in the sealing section (10) an annular continuous sealing zone (13) is formed that directly adjoins an edge of the inert film (9) that envelopes the piston section (8), the sealing zone in a working position abutting against the syringe or carpule cylinder (1).

2. The method according to claim 1, wherein during the forming operation at least one annular continuous sealing lip (II) is formed on an outer circumference of the sealing section (10), and wherein the sealing lip (11) is displaced toward the receiving cavity (6) during the separating operation.

3. The method according to claim 1, wherein in the separating operation the at least one piston section (8) is placed centered into an opening (28) of a cutting die (27) and the flange (16) bordering the piston stopper (2) is clamped between the cutting die (27) and a clamping plate (29), wherein a portion of the sealing section (10) which projects beyond the flange (16) engages a pass-through opening (30) provided in the clamping plate (29), and wherein afterwards the wall region of the sealing section (10) bordering the receiving cavity (6) of the piston stopper (2) is displaced by a cutting punch (32) into the receiving cavity (6) and the flange (16) is blanked off the piston stopper (2).

4. The method according to claim 3, wherein the cutting punch (32) is moved in a direction from the free end of the sealing section (10) toward the flange (16) to separate the piston stopper (2) from the flange (16).

5. The method according claim 1, wherein the rubber sheet (7) is continuously sealed on its outer edge against at least one die plate (14, 15) of the forming tool on which it rests, and wherein during and/or after the opening of the forming tool to release the vulcanized layered arrangement from the die plate (14, 15) a gas is injected between the die plate and the layered arrangement.

6. The method according to claim 5, wherein the step of sealing the vulcanized layered arrangement against the die plate (14, 15) during the forming operation comprises forming a seal on an outer edge of the layered arrangement (22), the seal tightly abutting against the die plate (14, 15) and being continuous around the layered arrangement.

* * * * *